(12) United States Patent
Poirot et al.

(10) Patent No.: US 9,447,141 B2
(45) Date of Patent: Sep. 20, 2016

(54) PROCESS FOR THE PREPARATION OF STEROL DERIVATIVES

(71) Applicants: INSERM (Institut National de la Sante et de la Recherche Medicale), Paris (FR); Affichem, Toulouse (FR)

(72) Inventors: Marc Poirot, Toulouse (FR); Michael Paillasse, Toulouse (FR); Philippe De Medina, Toulouse (FR); Sandrine Poirot, Toulouse (FR)

(73) Assignee: (INSERM) (Institut National de la Sante et de la Recherche Medicale), Paris (FR)

( * ) Notice: Subject to any disclaimer, the term of this patent is extended or adjusted under 35 U.S.C. 154(b) by 0 days.

(21) Appl. No.: 14/359,658

(22) PCT Filed: Nov. 23, 2012

(86) PCT No.: PCT/EP2012/073489
§ 371 (c)(1),
(2) Date: May 21, 2014

(87) PCT Pub. No.: WO2013/076257
PCT Pub. Date: May 30, 2013

(65) Prior Publication Data
US 2014/0309417 A1 Oct. 16, 2014

(30) Foreign Application Priority Data
Nov. 24, 2011 (EP) .................................... 11306548

(51) Int. Cl.
*C07J 43/00* (2006.01)
*C07J 41/00* (2006.01)
*C07J 71/00* (2006.01)

(52) U.S. Cl.
CPC ........... *C07J 43/003* (2013.01); *C07J 41/0005* (2013.01); *C07J 71/001* (2013.01)

(58) Field of Classification Search
CPC ..... C07J 43/00; C07J 43/003; C07J 41/0005
USPC .......................................... 540/108; 552/515
See application file for complete search history.

(56) References Cited

FOREIGN PATENT DOCUMENTS

WO          03/089449          10/2003

OTHER PUBLICATIONS

Carre et al, "A Convenient Preparation of B-Amino Alcohols From Epdxides and Halomagnesium Alkylamides," Tetrahedron Letters, 26(26):3107-3110 (1985).
Chini et al., "Efficient Metal Salt Catalyzed Azidolysis of Epoxides With Sodium Azide in Acetonitrile," Tetrahedron Letters, 31(39):5641-5644 (1990).
Chini et al. "Lanthanide(III) Trifluoromethanesulfonates as Extraordinarily Effective New Catalysts for the Aminolysis of 1,2-Epoxides," Tetrahedron Letters, 35(3):433-436 (1994).
Chini et al., "Metal Salts as New Catalysts for Mild and Efficient Aminolysis of Oxiranes," Tetrahedron Letters, 31(32):4661-4664 (1990).
De Medina et al., "Synthesis of New Alkylarninooxysterols with Potent Cell Differentiating Activities: Identification of Leads of the Treatment of Cancer and Neuredegerierative Diseases," J. Med. Chem., 52:7765-7777 (2009) XP002673411.
Fujiwara et al.,"Tetraphenylstibonium Triflate as a Regio- and Chemoselective Catalyst in the Reaction of Oxiranes With Amines." Tetrahedron Letters, 30(6)739-742 (1989).
International Search Report in PCT/EP2012/073489 dated Dec. 18, 2012.
Yamada et al., "Aminolead Compounds as a New Reagent for Regioselective Ring Opening of Epoxides," Tetrahedron Letters; 30(32):4255-4258 (1989).

*Primary Examiner* — T. Victor Oh
(74) *Attorney, Agent, or Firm* — McAndrews, Held and Malloy

(57) ABSTRACT

The present invention relates to a process for the preparation of sterol derivatives comprising the reaction of an α-epoxy compound with an amine in an alcohol comprising 3 to 5 carbon atoms as a solvent.

15 Claims, No Drawings

PROCESS FOR THE PREPARATION OF STEROL DERIVATIVES

The present application is filed pursuant to 35 U.S.C. 371 as a U.S. National Phase application of International Patent Application No. PCT/EP2012/073489, which was filed Nov. 23, 2012, claiming the benefit of priority to European Patent Application No. 11306548.6, which was filed on Nov. 24, 2011. The entire text of the aforementioned applications is incorporated herein by reference in its entirety.

The present invention relates to a process for the preparation of sterol derivatives comprising the reaction of an α-epoxy compound with an amine in an alcohol comprising 3 to 5 carbon atoms as a solvent.

Alkylaminoxysterols are potent inductors of cell differentiation at low doses (de Medina et al., *J. Med. Chem.*, 2009).

Among this class of compounds, the most potent molecules appear to be Dendrogenin A and Dendrogenin B of which formulas are represented below:

Dendrogenin A

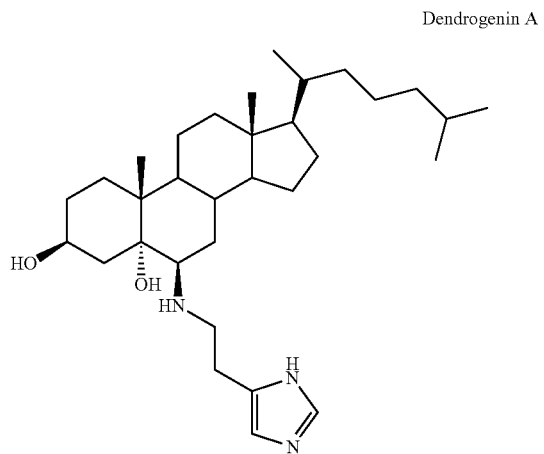

Dendrogenin B

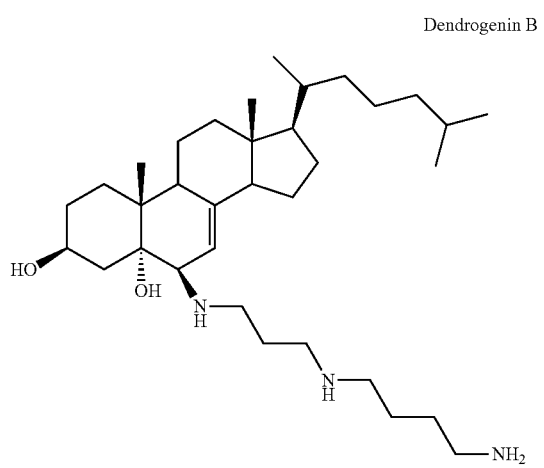

De Medina et al. disclose the synthesis of Dendrogenin A and Dendrogenin B, and of other 6β-aminoalkyloxysterols, in two steps:

Chart 1

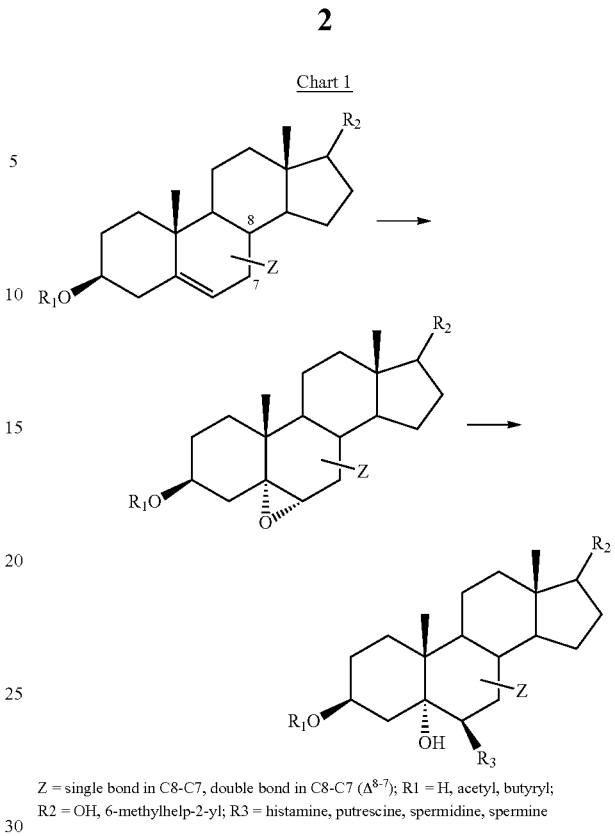

Z = single bond in C8-C7, double bond in C8-C7 ($\Delta^{8-7}$); R1 = H, acetyl, butyryl;
R2 = OH, 6-methylhelp-2-yl; R3 = histamine, putrescine, spermidine, spermine The first step consists in the 5,6-epoxidation of a sterol or steroid. Accordingly, meta-chloroperbenzoic acid (mCPBA) in methylene chloride is reacted with a sterol or steroid in methylene chloride at room temperature. This step leads to the synthesis of a 5,6-epoxide compound as shown in chart 1.

The second step consists in the aminolysis of the 5,6-epoxide compound. Accordingly, a solution of the 5,6-epoxide compound obtained in the first step in anhydrous ethanol is reacted with an amine (histamine, putrescine, spermidine or spermine) as a free base dissolved in anhydrous ethanol in the presence of lithium perchlorate as a catalyst. This step leads to the synthesis of a 6β-aminoalkyloxysterol as shown in chart 1.

WO03/089449 also discloses a process for the preparation of sterol derivatives, in particular 6β-aminoalkyloxysterols, comprising an epoxidation in a first step and an aminolysis in a second step. In the aminolysis step, the epoxide compound obtained in the first step, dissolved in a solvent C, is reacted with an amine, dissolved in a solvent E that is miscible with solvent C, in the presence of an activator D (lithium perchlorate). Only anhydrous ethanol and pyridine are disclosed as solvent C. Moreover, the use of the activator to perform the aminolysis of the 5,6-epoxide is necessary.

Aminolysis of epoxides are also described in other publications.

Carre et al. (*Tetrahedron Lett.* 1985, 26, 3107-3110) disclose the preparation of β-aminoalcohols from epoxides and halomagnesium alkylamides in THF, a polar aprotic solvent.

Fujiwara et al. (*Tetrahedron Lett.* 1989, 30, 739-742) disclose the nucleophilic addition of amines to oxiranes in the presence of a catalytic amount of tetraphenylstibonium triflate. Various solvents are used such as methanol and dichloromethane. Fujiwara et al. report that a protic solvent (such as methanol) was not appropriate for their reaction.

Therefore, the formation of aminoalcohols could be accomplished under aprotic conditions only (such as dichloromethane).

Yamada et al. (*Tetrahedron Lett.* 1989, 30, 4255-4258) disclose a regioselective ring opening of epoxides by using aminolead compounds. All reactions are carried out in ether as a solvent.

Chini et al. (*Tetrahedron Lett.* 1990, 31, 4661-4664) disclose the aminolysis of oxiranes (1,2-epoxides) with a variety of amines by using metal salts as catalysers. The aminolysis is carried out in various solvents, either non-protic solvents (acetonitrile or acetone) or apolar solvents (toluene or ether).

Chini et al. (*Tetrahedron Lett.* 1990, 39, 5641-5644) disclose the metal salt catalyzed azidolysis of epoxides with sodium azide in acetonitrile, a low polarity non-protic solvent). Chini et al. report that acetonitrile appears to offer considerable advantages compared with the other methodologies using in particular protic solvents such as methanol.

Chini et al. (*Tetrahedron Lett.* 1994, 35, 433-436) disclose lanthanides (III) trifluoromethanesulfonates (triflates), such as $Yb(OTf)_3$, $Nd(OTf)_3$ and $Gd(OTf)_3$, catalyse in a very efficient way the aminolysis of 1,2-epoxides, affording the corresponding β-amino alcohols, at room temperature and in low polar non-protic solvents (dichloromethane or toluene) in very good yields.

The present invention aims to provide a process for the preparation of sterol derivatives, in particular 6β-aminoalkyloxysterols, wherein the yield of the aminolysis of the 5,6-epoxide compound is increased compared to the yield of the aminolysis described in the prior art.

This goal is attained by using an alcohol comprising 3 to 5 carbon atoms or a mixture thereof as a solvent for the aminolysis of the epoxide by the amine.

In comparison with the process disclosed by de Medina et al wherein ethanol is used as a solvent, the process of the invention has the following advantages:

less volume of solvent is used (up to 8 times lower)

the use of a catalyst, such as metallic catalysts, to promote the aminolysis is not necessary to obtain good yields, the reaction time is faster, the yields are increased, it is less expensive, it has a lower impact on the environment.

These advantages are unexpected considering the previously cited prior art which motivates the skilled person to use non-protic solvents, such as THF, dichloromethane, acetonitrile or toluene.

Furthermore, with respect to the process disclosed by De Medina et al. (2009), it is totally unexpected that increased yields would be obtained with an alcohol comprising 3 to 5 carbon atoms, even without a catalyst in the reaction medium. This advantage is significant because the catalyst used in De Medina et al. (lithium perchlorate) is toxic. Therefore, the process of the invention has a lower impact on the environment and is safer from a clinical point of view.

Process of Preparation of Sterol Derivatives of Formula (I)

The present invention hence relates to a process for the preparation of a compound of formula (I):

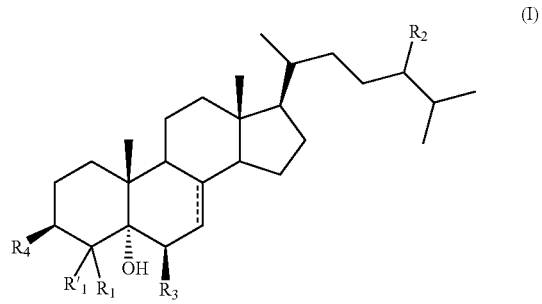

wherein:
The dotted line denotes a bond which is single or double,
—R1 and R'1 are the same or different and represent H or $CH_3$,
—R2 is H, $CH_3$ or $C_2H_5$,
—R3 is —NRR' wherein R and R' are the same or different and are selected from the group consisting of:
—H,
—$(CH_2)_n$-OH wherein
n is an integer comprised between 1 and 4,
—$(CH_2)_n$-NHP wherein
n is an integer comprised between 1 and 6 and
P is H or a protecting group;
—$(CH_2)_n$-NP—$(CH_2)_m$-NHP' wherein
n is an integer comprised between 1 and 6,
m is an integer comprised between 1 and 6, and
P and P' are the same or different and represent H or a protecting group;
—$(CH_2)_n$-NP—$(CH_2)_m$-NP'—$(CH_2)_p$-NHP'''
wherein
n is an integer comprised between 1 and 6,
m is an integer comprised between 1 and 6,
p is an integer comprised between 1 and 6, and
P, P' and P''' are the same or different and represent H or a protecting group;
—$(CH_2)_n$-X wherein
n is an integer comprised between 1 and 4 and
X=imidazol, indol or phenyl, optionally substituted with one or several groups chosen among OH, $NH_2$ or SH.
—R4 is OH, acetoxy or butoxy,
said process comprising:
(a) reacting an α-epoxy compound of formula (II):

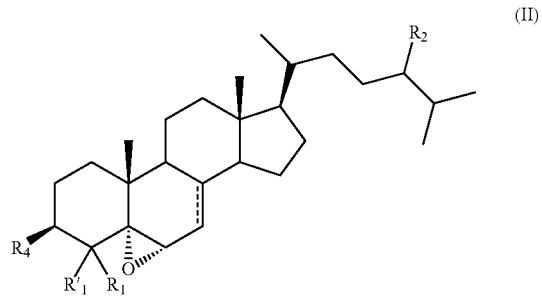

wherein R1, R'1, R2 and R4 have the same meaning than in formula (I) and the dotted line denotes a bond which is single or double, with a monoamine or polyamine of formula (III):

R3H (III)

wherein R3 has the same meaning than in formula (I), in a reaction medium at reflux;
(b) recovering compound (I) from the reaction medium; wherein an alcohol comprising 3 to 5 carbon atoms or a mixture thereof is used as a solvent in the reaction medium.

If desired, compound (I) may be reacted with a deprotecting agent in order to remove the protecting group(s) present in the molecule.

Therefore, another object of the present invention is a process for the preparation of a compound of formula (I) as defined above, wherein the compound recovered from step b) contains at least one amino protecting group and is further reacted with a deprotecting agent so as to remove said amino protecting group from the compound.

"Protecting group" refers to a grouping of atoms that when attached to a reactive group in a molecule masks, reduces or prevents that reactivity. Examples of protecting groups can be found in T. W. Green and P. G. M. Wuts, Protective Groups in Organic Chemistry, (John Wiley and sons, 1991) and Harrison and Harrison et al., Compendium of Synthetic Organic Methods, Vols. 1-8 (John Wiley and Sons, 1971-1996).

Representative amino protecting groups include formyl, acetyl, trifluoroacetyl, benzyl, benzyloxycarbonyl (CBZ), ter-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

The Amine of Formula (III)

The amine of formula (III) is preferably a monoamine or polyamine of formula NHR wherein R is selected from the group consisting of:
—(CH$_2$)n-OH wherein
  n is an integer comprised between 1 and 4,
—(CH$_2$)n-NHP wherein
  n is an integer comprised between 1 and 6 and
  P is H or a protecting group;
—(CH$_2$)n-NP—(CH$_2$)m-NHP' wherein
  n is an integer comprised between 1 and 6,
  m is an integer comprised between 1 and 6, and
  P and P' are the same or different and represent H or a protecting group;
—(CH$_2$)n-NP—(CH$_2$)m-NP'—(CH$_2$)p-NHP''' wherein
  n is an integer comprised between 1 and 6,
  m is an integer comprised between 1 and 6,
  p is an integer comprised between 1 and 6, and
  P, P' and P''' are the same or different and represent H or a protecting group;
—(CH$_2$)n-X wherein
  n is an integer comprised between 1 and 4 and
  X=imidazol, indol or phenyl, optionally substituted with one or several groups chosen among OH, NH$_2$ or SH.

The amine of formula (III) is more preferably a monoamine or polyamine of formula NHR wherein R is selected from the group consisting of:
—(CH$_2$)n-OH wherein
  n is an integer comprised between 1 and 4,
—(CH$_2$)n-NHP wherein
  n is an integer comprised between 1 and 4 and
  P is H or a protecting group;
—(CH$_2$)n-NP—(CH$_2$)m-NHP' wherein
  n is an integer comprised between 1 and 4,
  m is an integer comprised between 1 and 4, and
  P and P' are the same or different and represent H or a protecting group;
—(CH$_2$)n-NP—(CH$_2$)m-NP'—(CH$_2$)p-NHP''' wherein
  n is an integer comprised between 1 and 4,
  m is an integer comprised between 1 and 4,
  p is an integer comprised between 1 and 4, and
  P, P' and P''' are the same or different and represent H or a protecting group;
—(CH$_2$)n-X wherein
  n is an integer comprised between 1 and 4 and
  X=imidazol, indol or phenyl, optionally substituted with one or several groups chosen among OH, NH$_2$ or SH.

More preferably, the amine of formula (III) is chosen among histamine, spermidine, spermine, putrescine, ethanolamine, diaminopropylamine, diaminobutylamine, tryptamine, serotonin, 1,3-diaminopropane, or N$^1$,N$^8$-di-tert-butyloxycarbonylspermidine.

The Epoxy Compounds of Formula (II)

Compound of formula (II) is preferably chosen among cholestan-5α,6α-epoxy-3β-ol, cholest-7-en-5α,6α-epoxy-3β-ol, sitostan-5α,6α-epoxy-3β-ol, campestan-5α,6α-epoxy-3β-ol, 3β-acetoxy-cholestan-5α,6α-epoxide, 3β-acetoxy-sitostan-5α,6α-epoxide or 3β-acetoxy-campestan-5α,6α-epoxide.

The Sterol Derivatives of Formula (I)

The process of the invention allows for instance to synthesize the following compounds of formula (I):
5α-hydroxy-6β-[2-(1H-imidazol-4-yl)ethylamino]cholestan-3β-ol (Dendrogenin A),
5α-hydroxy-6β-[2-(1H-imidazol-4-yl)ethylamino]campestan-3β-ol,
5α-hydroxy-6β-[2-(1H-imidazol-4-yl)ethylamino]sitostan-3β-ol,
3β-acetoxy-5α-hydroxy-6β-[2-(1H-imidazol-4-yl)ethylamino]cholestane,
3β-acetoxy-5α-hydroxy-6β-[2-(1H-imidazol-4-yl)ethylamino]campestane,
3β-acetoxy-5α-hydroxy-6β-[2-(1H-imidazol-4-yl)ethylamino]sitostane,
5α-hydroxy-6β-[2-(1H-indol-3-yl)ethylamino]cholestan-3β-ol,
5α-hydroxy-6β-[2-(1H-indol-3-yl)ethylamino]campestan-3β-ol,
5α-hydroxy-6β-[2-(1H-indol-3-yl)ethylamino]sitostan-3β-ol,
5α-hydroxy-6β-[2-(1H-indol-3-yl)ethylamino]cholest-7-en-3β-ol,
3β-acetoxy-5α-hydroxy-6β-[2-(1H-indol-3-yl)ethylamino]cholestane,
3β-acetoxy-5α-hydroxy-6β-[2-(1H-indol-3-yl)ethylamino]campestane,
3β-acetoxy-5α-hydroxy-6β-[2-(1H-indol-3-yl)ethylamino]sitostane,
3β-acetoxy-5α-hydroxy-6β-[2-(1H-indol-3-yl)ethylamino]cholest-7-ene,
5α-hydroxy-6β-[2-(1H-indol-3-yl-5-ol)ethylamino]cholestan-3β-ol,
5α-hydroxy-6β-[2-(1H-indol-3-yl-5-ol)ethylamino]cholest-7-en-3β-ol,
5α-hydroxy-6β-[2-(1H-indol-3-yl-5-ol)ethylamino]campestan-3β-ol,
5α-hydroxy-6β-[2-(2-(1H-indol-3-yl-5-ol)ethylamino]sitostan-3β-ol, 3β-acetoxy-5α-hydroxy-6β-[2-(2-(1H-indol-3-yl-5-ol)eth-ylamino]cholestane,
3β-acetoxy-5α-hydroxy-6β-[2-(1H-indol-3-yl-5-ol)ethyl-amino]cholest-7-ene,
3β-acetoxy-5α-hydroxy-6β-[2-(2-(1H-indol-3-yl-5-ol)eth-ylamino]campestane,
3β-acetoxy-5α-hydroxy-6β-[2-(1H-indol-3-yl-5-ol)ethyl-amino]sitostane,
5α-hydroxy-6β-[3-(4-aminobutylamino)propylamino]cholest-7-en-3β-ol (Dendrogenin B),
5α-hydroxy-6β-[4-(3-aminopropylamino)butylamino]cholest-7-en-3β-ol,
5α-hydroxy-6β-[3-(4-aminobutylamino)propylamino]cholestan-3β-ol,
5α-hydroxy-6β-[4-(3-aminopropylamino)butylamino]cholestan-3β-ol,
5α-hydroxy-6β-[3-(4-aminobutylamino)propylamino]campestan-3β-ol,
5α-hydroxy-6β-[4-(3-aminopropylamino)butylamino]campestan-3β-ol,
5α-hydroxy-6β-[3-(4-aminobutylamino)propylamino]sitostan-3β-ol,
5α-hydroxy-6β-[4-(3-aminopropylamino)butylamino]sitostan-3β-ol,
5α-hydroxy-6β-[(4-aminobutyl)(3-aminopropyl)amino]cholest-7-en-3β-ol,
5α-hydroxy-6β-[(4-aminobutyl)(3-aminopropyl)amino]cholestan-3β-ol,
5α-hydroxy-6β-[(4-aminobutyl)(3-aminopropyl)amino]campestan-3β-ol,
5α-hydroxy-6β-[(4-aminobutyl)(3-aminopropyl)amino]sitostan-3β-ol,
5α-hydroxy-6β-{3-[4-(3-aminopropylamino)butylamino]propylamino}cholest-7-en-3β-ol,
5α-hydroxy-6β-{3-[4-(3-aminopropylamino)butylamino]propylamino}cholestan-3β-ol,
5α-hydroxy-6β-{3-[4-(3-aminopropylamino)butylamino]propylamino}campestan-3β-ol,
5α-hydroxy-6β-{3-[4-(3-aminopropylamino)butylamino]propylamino}sitostan-3β-ol,
5α-hydroxy-6β-(4-aminobutylamino)cholest-7-en-3β-ol,
5α-hydroxy-6β-(4-aminobutylamino)cholestan-3β-ol,
5α-hydroxy-6β-(4-aminobutylamino)campestan-3β-ol,
5α-hydroxy-6β-(4-aminobutylamino)sitostan-3β-ol,
5α-hydroxy-6β-(3-aminopropylamino)cholest-7-en-3β-ol,
5α-hydroxy-6β-(3-aminopropylamino)cholestan-3β-ol,
5α-hydroxy-6β-(3-aminopropylamino)campestan-3β-ol,
5α-hydroxy-6β-(3-aminopropylamino)sitostan-3β-ol,
3β-acetoxy-5α-hydroxy-6β-[3-(4-aminobutylamino)propylamino]cholest-7-ene,
3β-acetoxy-5α-hydroxy-6β-[4-(3-aminopropylamino)butylamino]cholest-7-ene,
3β-acetoxy-5α-hydroxy-6β-[3-(4-aminobutylamino)propylamino]cholestane,
3β-acetoxy-5α-hydroxy-6β-[4-(3-aminopropylamino)butylamino]cholestane,
3β-acetoxy-5α-hydroxy-6β-[3-(4-aminobutylamino)propylamino]campestane,
3β-acetoxy-5α-hydroxy-6β-[4-(3-aminopropylamino)butylamino]campestane,
3β-acetoxy-5α-hydroxy-6β-[3-(4-aminobutylamino)propylamino]sitostane,
3β-acetoxy-5α-hydroxy-6β-[4-(3-aminopropylamino)butylamino]sitostane,
3β-acetoxy-5α-hydroxy-6β-[(4-aminobutyl)(3-aminopropyl)amino]cholest-7-ene,
3β-acetoxy-5α-hydroxy-6β-[(4-aminobutyl)(3-aminopropyl)amino]cholestane,
3β-acetoxy-5α-hydroxy-6β-[(4-aminobutyl)(3-aminopropyl)amino]campestane,
3β-acetoxy-5α-hydroxy-6β-[(4-aminobutyl)(3-aminopropyl)amino]sitostane,
3β-acetoxy-5α-hydroxy-6β-{3-[4-(3-aminopropylamino)butylamino]propylamino}cholest-7-ene,
3β-acetoxy-5α-hydroxy-6β-{3-[4-(3-aminopropylamino)butylamino]propylamino}cholestane,
3β-acetoxy-5α-hydroxy-6β-{3-[4-(3-aminopropylamino)butylamino]propylamino}campestane,
3β-acetoxy-5α-hydroxy-6β-{3-[4-(3-aminopropylamino)butylamino]propylamino}sitostane,
3β-acetoxy-5α-hydroxy-6β-(4-aminobutylamino)cholest-7-ene,
3β-acetoxy-5α-hydroxy-6β-(4-aminobutylamino)cholestane,
3β-acetoxy-5α-hydroxy-6β-(4-aminobutylamino)campestane,
3β-acetoxy-5α-hydroxy-6β-(4-aminobutylamino)sitostane,
3β-acetoxy-5α-hydroxy-6β-(3-aminopropylamino)cholest-7-ene,
3β-acetoxy-5α-hydroxy-6β-(3-aminopropylamino)cholestane,
3β-acetoxy-5α-hydroxy-6β-(3-aminopropylamino)campestane, or
3β-acetoxy-5α-hydroxy-6β-(3-aminopropylamino)sitostane.

DETAILED DESCRIPTION OF THE PROCESS

According to the invention, step (a) comprises the aminolysis of an α-epoxy compound of formula (II) as defined above with an amine of formula (III) as defined above.

The aminolysis is carried out in an alcohol comprising 3 to 5 carbon atoms or a mixture thereof as a solvent, at reflux. Under these conditions, the yield of the aminolysis is significantly increased compared to the same reaction in ethanol as a solvent, even without using a catalyst.

The nature and the amount of solvent in the aminolysis is preferably chosen so as to allow complete dissolution of the reactants (i.e. the amine of formula (III) and the α-epoxy compound of formula (II) as defined above) at the boiling temperature.

In practice, the aminolysis may be carried out by adding the amine of formula (III) dissolved in an alcohol comprising 3 to 5 carbon atoms or a mixture thereof to a solution of the α-epoxy compound of formula (II) in the same or different alcohol comprising 3 to 5 carbon atoms or a mixture thereof, preferably in the same alcohol. The aminolysis may be also carried out by simply adding the alcohol comprising 3 to 5 carbon atoms or a mixture thereof to the reactants charged in a flask or reactor beforehand.

Typically, four to six volumes of solvent, preferably five volumes of solvent are added to one volume of the reactants to carry out the aminolysis. In comparison, when if ethanol is used as a solvent, 40 volumes of solvent are necessary to obtain similar yields.

The reaction medium may contain a minor amount of solvents which come from the reactants themselves and are not C3-C5 alcohols. For instance, when the amine of formula (II) is ethanolamine, it is used as a reactant and solvent in the reaction medium.

The alcohol used as a solvent in the reaction medium is an alcohol comprising 3 to 5 carbon atoms or a mixture thereof, thereby including propanol, butanol, pentanol, and mixtures thereof. Propanol includes 1-propanol, or 2-propanol. Butanol includes 1-butanol, or 2-butanol and 2-methyl-propan-2-ol. Pentanol includes 1-pentanol, 2-pentanol, or 3-pentanol. Preferably, the alcohol is chosen among 1-propanol, 1-butanol or 2-butanol, or a mixture thereof.

According to the invention, the aminolysis of step (a) is carried out at reflux. The reaction medium is preferably stirred to improve the reaction.

According to the invention, the aminolysis of step (a) may be carried out with or without a catalyst. Preferably, it is carried out without a catalyst because it appears that the presence of a catalyst does not increase the yield of the aminolysis.

If a catalyst is used to perform the aminolysis of step (a), it may be chosen among Lewis acids, such as $LiClO_4$, $Sc(OTf)_3$, $Yb(OTf)_3$ or $Ca(Otf)_2$. Preferably, the catalyser will be $Ca(Otf)_2$.

Under reflux and stirring, the aminolysis of step (a) can be completed with a yield of 100% in 18 hours with 4 equivalents of amine or 40 hours with 2 equivalents of amine in 5 volumes of 1-butanol. In comparison, the same reaction carried out with ethanol will be completed in 120-144 hours with 4 equivalents of amine with a yield of from 12% to 25%. Use of catalysts in 1-butanol at reflux does not reduce significantly the reaction time.

The use of an alcohol comprising 3 to 5 carbon atoms or a mixture thereof as a solvent in the reaction medium reduces the reaction time compared to the same reaction with ethanol. It allows the reaction to be completed with a yield up to 100% within few hours.

According to the process of the invention, yields of up to 100% may be obtained from step (a).

When the amine of formula (III) is a polyamine containing several nucleophilic amino groups, such as spermidine, it may be necessary to protect one or several of these amino groups in order to avoid mixtures of regioisomers. For instance, one or two of the 3 amino groups of spermidine may be protected with Boc protecting groups, as described in de Medina et al. The deprotection of the amines can be done after aminolysis with an appropriate deprotecting agent (such as trifluoroacetic acid) to obtain the expected free amines of formula (I).

Amino protecting groups or amino deprotecting agents and methods to protect or deprotect amino groups are disclosed in T. W. Green and P. G. M. Wuts, Protective Groups in Organic Chemistry, (John Wiley and sons, 1991) and Harrison and Harrison et al., Compendium of Synthetic Organic Methods, Vols. 1-8 (John Wiley and Sons, 1971-1996). For instance, amino groups may be protected by reaction with Boc2O in DCM or with BocON in THF (see de Medina et al). Protected groups may be deprotected by reaction with TFA; $Bu_4N^+F^-$; $KF.H_2O$, $CH_3CN$, 50° C.; HCl 3M, EtOAc, 25° C.; $Me_3SiI$, $CH_3CN$ or $CHCl_3$, 25° C.

Once step (a) is finished, compound (I) is recovered from the reaction medium. For example, the solvent of the reaction medium is evaporated. The residue may be diluted in a solvent, such as ethyl acetate, washed with water and dried.

The recovered crude product may be purified by recristallisation in the appropriate solvent, by liquid chromatography or by filtration through silica pad.

Process of Preparation of α-Epoxy Compounds of Formula (II)

The α-epoxy compound of formula (II)

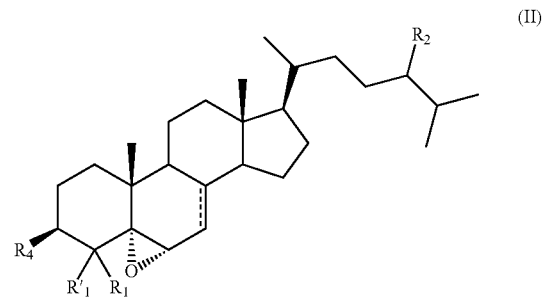

as defined above may be obtained by:
a) reacting meta-chloroperoxybenzoic acid with a compound of formula (IV):

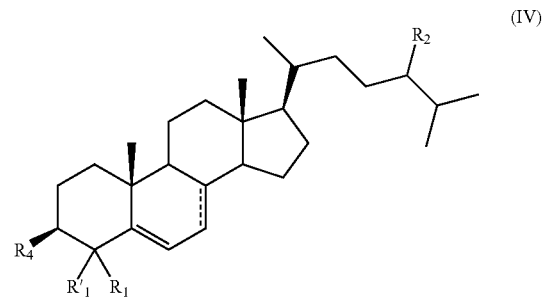

wherein R1, R'1, R2 and R4 have the same meaning than in formula (I) above and the dotted line denotes a bond which is single or double;

b) recovering said α-epoxy compound of formula (II).

Therefore, an object of the invention is also a process for the preparation of a compound of formula (I) as defined above, comprising the following steps:
a) reacting meta-chloroperoxybenzoic acid with a compound of formula (IV):

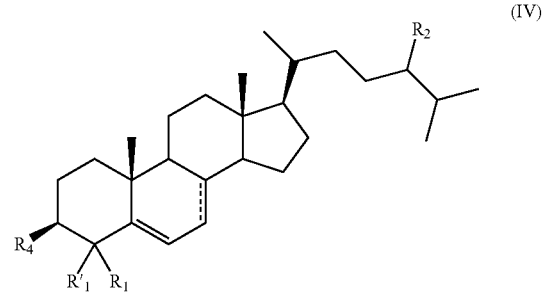

wherein R1, R'1, R2 and R4 have the same meaning than in formula (I) above and the dotted line denotes a bond which is single or double, to obtain an α-epoxy compound of formula (II):

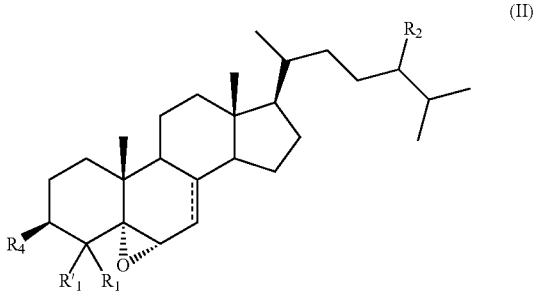

(II)

b) recovering said α-epoxy compound of formula (II),
c) reacting said α-epoxy compound of formula (II) with an amine of formula (III):

R3H  (III)

wherein R3 has the same meaning than in formula (I), in a reaction medium at reflux,
wherein an alcohol comprising 3 to 5 carbon atoms or a mixture thereof is used as a solvent in the reaction medium.
d) recovering compound (I) from the reaction medium.

According to the invention, compound (IV) is preferably chosen among cholesterol, sitosterol, campesterol, 7-dehydrocholesterol, 7-dehydrosisterol or 7-dehydrocampesterol.

EXAMPLES

Example 1

5,6α-epoxicholest-7-en-3β-ol (8.9 g, 22.1 mmol, 1 eq) and spermidine (6.4 g, 44.1 mmol, 2 eq) were charged in a round-bottomed flask equipped with a magnetic stirrer bar. 1-Butanol (70 ml, 5 vol) was added and the mixture heated to reflux for 40 h. The reaction mixture was cooled at r.t., diluted with methyl-tertbutyl-ether (5 vol) and washed with water (5 vol) and with brine (5 vol). The organic layer was passed through a silica pad (40 g) eluted with methyl-tertbutyl-ether (3 vol) then 10% Methanol/ethyl acetate (60 vol). Fractions of interest were pooled and the solvent was removed under reduced pressure to give Dendrogenin B (5α-Hydroxy-6β-[4-(3-aminopropylamino)-butylamino]-cholest-7-en-3β-ol) as a white solid (7.0 g, 58%). In same conditions, use of ethanol as solvent (40 vol) and Ca(OTf)$_2$ as catalyst gave a 14% yield.

Example 2

5,6α-epoxicholestan-3β-ol epoxide (8.9 g, 22.1 mmol, 1 eq) and histamine (4.9 g, 44.1 mmol, 2 eq) were charged in a round-bottomed flask equipped with a magnetic stirrer bar. 1-Butanol (70 ml, 5 vol) was added and the mixture heated to reflux for 40 h. The reaction mixture was cooled at r.t., diluted with methyl-tertbutyl-ether (5 vol) and washed with water (5 vol) and with brine (5 vol). The organic layer was passed through a silica pad (40 g) eluted with methyl-tertbutyl-ether (3 vol) then 10% Methanol/ethyl acetate (60 vol). Fractions of interest were pooled and the solvent was removed under reduced pressure to give Dendrogenin A (5α-Hydroxy-6β-[2-(1H-imidazol-4-yl)-ethylamino]-cholestan-3β-ol) as a white solid (6.8 g, 60%). In same conditions, use of ethanol as solvent (40 vol) and Ca(OTf)$_2$ as catalyst gave a 17% yield.

Example 3

5,6α-epoxicholest-7-en-3β-ol (8.9 g, 22.1 mmol, 1 eq) and spermine (8.9 g, 44.1 mmol, 2 eq) were charged in a round-bottomed flask equipped with a magnetic stirrer bar. 1-Butanol (70 ml, 5 vol) was added and the mixture heated to reflux for 40 h. The reaction mixture was cooled at r.t., diluted with methyl-tertbutyl-ether (5 vol) and washed with water (5 vol) and with brine (5 vol). The organic layer was passed through a silica pad (40 g) eluted with methyl-tertbutyl-ether (3 vol) then 10% Methanol/ethyl acetate (60 vol). Fractions of interest were pooled and the solvent was removed under reduced pressure to give 5α-Hydroxy-6β-N-{3-[4-(3-Amino-propylamino)-butylamino]-propylamino}-cholest-7-en-3β-ol as a light yellow solid (7.4 g, 48%). In same conditions, use of ethanol as solvent (40 vol) and Ca(OTf)$_2$ as catalyst gave a 8% yield.

Example 4

5,6α-epoxicholestan-3β-ol (8.9 g, 22.1 mmol, 1 eq) and spermidine (6.4 g, 44.1 mmol, 2 eq) were charged in a round-bottomed flask equipped with a magnetic stirrer bar. 1-Butanol (70 ml, 5 vol) was added and the mixture heated to reflux for 40 h. The reaction mixture was cooled at r.t., diluted with methyl-tertbutyl-ether (5 vol) and washed with water (5 vol) and with brine (5 vol). The organic layer was passed through a silica pad (40 g) eluted with methyl-tertbutyl-ether (3 vol) then 10% Methanol/ethyl acetate (60 vol). Fractions of interest were pooled and the solvent was removed under reduced pressure to give 5α-Hydroxy-6β-[4-(3-aminopropylamino)-butylamino]-cholestan-3β-ol as a light yellow solid (6.1 g, 50%). In same conditions, use of ethanol as solvent (40 vol) and Ca(OTf)$_2$ as catalyst gave a 11% yield.

Example 5

5,6α-epoxicholestan-3β-ol (8.9 g, 22.1 mmol, 1 eq) and putrescine (3.9 g, 44.1 mmol, 2 eq) were charged in a round-bottomed flask equipped with a magnetic stirrer bar. 1-Butanol (70 ml, 5 vol) was added and the mixture heated to reflux for 40 h. The reaction mixture was cooled at r.t., diluted with methyl-tertbutyl-ether (5 vol) and washed with water (5 vol) and with brine (5 vol). The organic layer was passed through a silica pad (40 g) eluted with methyl-tertbutyl-ether (3 vol) then 10% Methanol/ethyl acetate (60 vol). Fractions of interest were pooled and the solvent was removed under reduced pressure to give 5α-Hydroxy-6β-(4-aminobutylamino)-cholestan-3β-ol as a white solid (6.6 g, 61%). In same conditions, use of ethanol as solvent (40 vol) and Ca(OTf)$_2$ as catalyst gave a 19% yield.

Example 6

5,6α-epoxicholestan-3β-ol (8.9 g, 22.1 mmol, 1 eq) and 1,3-diaminopropane (3.3 g, 44.1 mmol, 2 eq) were charged in a round-bottomed flask equipped with a magnetic stirrer bar. 1-Butanol (70 ml, 5 vol) was added and the mixture heated to reflux for 40 h. The reaction mixture was cooled at r.t., diluted with methyl-tertbutyl-ether (5 vol) and washed with water (5 vol) and with brine (5 vol). The organic layer was passed through a silica pad (40 g) eluted with methyl-tertbutyl-ether (3 vol) then 10% Methanol/ethyl acetate (60 vol). Fractions of interest were pooled and the solvent was removed under reduced pressure to give 5α-Hydroxy-6β-(3-aminopropylamino)-cholestan-3β-ol as a white solid (6.3 g, 60%). In same conditions, use of ethanol as solvent (40 vol) and Ca(OTf)$_2$ as catalyst gave a 20% yield.

Example 7

5,6α-epoxicholestan-3β-ol (8.9 g, 22.1 mmol, 1 eq) and tryptamine (7.1 g, 44.1 mmol, 2 eq) were charged in a round-bottomed flask equipped with a magnetic stirrer bar. 1-Butanol (70 ml, 5 vol) was added and the mixture heated to reflux for 40 h. The reaction mixture was cooled at r.t., diluted with methyl-tertbutyl-ether (5 vol) and washed with water (5 vol) and with brine (5 vol). The organic layer was passed through a silica pad (40 g) eluted with methyl-tertbutyl-ether (3 vol) then 10% Methanol/ethyl acetate (60 vol). Fractions of interest were pooled and the solvent was removed under reduced pressure to give 5α-Hydroxy-6β-(3-propylamino)-cholestan-3β-ol as a white solid (7.3 g, 59%). In same conditions, use of ethanol as solvent (40 vol) and Ca(OTf)$_2$ as catalyst gave a 21% yield.

Example 8

5,6α-epoxicholest-7-en-3β-ol (8.9 g, 22.1 mmol, 1 eq) and putrescine (3.9 g, 44.1 mmol, 2 eq) were charged in a round-bottomed flask equipped with a magnetic stirrer bar. 1-Butanol (70 ml, 5 vol) was added and the mixture heated to reflux for 40 h. The reaction mixture was cooled at r.t., diluted with methyl-tertbutyl-ether (5 vol) and washed with water (5 vol) and with brine (5 vol). The organic layer was passed through a silica pad (40 g) eluted with methyl-tertbutyl-ether (3 vol) then 10% Methanol/ethyl acetate (60 vol). Fractions of interest were pooled and the solvent was removed under reduced pressure to give 5α-Hydroxy-6β-(4-aminobutylamino)-cholest-7-en-3β-ol as a white solid (6.9 g, 64%). In same conditions, use of ethanol as solvent (40 vol) and Ca(OTf)$_2$ as catalyst gave a 23% yield.

Example 9

5,6α-epoxicampestane-3β,17-diol (6.8 g, 22.1 mmol, 1 eq) and histamine (4.9 g, 44.1 mmol, 2 eq) were charged in a round-bottomed flask equipped with a magnetic stirrer bar. 1-Butanol (70 ml, 5 vol) was added and the mixture heated to reflux for 40 h. The reaction mixture was cooled at r.t., diluted with methyl-tertbutyl-ether (5 vol) and washed with water (5 vol) and with brine (5 vol). The organic layer was passed through a silica pad (40 g) eluted with methyl-tertbutyl-ether (3 vol) then 10% Methanol/ethyl acetate (60 vol). Fractions of interest were pooled and the solvent was removed under reduced pressure to give (5α-Hydroxy-6β-[2-(1H-imidazol-4-yl)-ethylamino]-campestane-3β,17-diol) as a white solid (5.7 g, 49%). In same conditions, use of ethanol as solvent (40 vol) and Ca(OTf)$_2$ as catalyst gave a 13% yield.

Example 10

5,6α-epoxisitostan-3β-ol (9.5 g, 22.1 mmol, 1 eq) and histamine (4.9 g, 44.1 mmol, 2 eq) were charged in a round-bottomed flask equipped with a magnetic stirrer bar. 1-Butanol (70 ml, 5 vol) was added and the mixture heated to reflux for 40 h. The reaction mixture was cooled at r.t., diluted with methyl-tertbutyl-ether (5 vol) and washed with water (5 vol) and with brine (5 vol). The organic layer was passed through a silica pad (40 g) eluted with methyl-tertbutyl-ether (3 vol) then 10% Methanol/ethyl acetate (60 vol). Fractions of interest were pooled and the solvent was removed under reduced pressure to give (5α-Hydroxy-6β-[2-(1H-imidazol-4-yl)-ethylamino]-sitostan-3β-ol) as a white solid (7.3 g, 61%). In same conditions, use of ethanol as solvent (40 vol) and Ca(OTf)$_2$ as catalyst gave a 11% yield.

Example 11

5,6α-epoxicholest-7-en-3β-ol (8.9 g, 22.1 mmol, 1 eq) and histamine (4.9 g, 44.1 mmol, 2 eq) were charged in a round-bottomed flask equipped with a magnetic stirrer bar. 1-Butanol (70 ml, 5 vol) was added and the mixture heated to reflux for 40 h. The reaction mixture was cooled at r.t., diluted with methyl-tertbutyl-ether (5 vol) and washed with water (5 vol) and with brine (5 vol). The organic layer was passed through a silica pad (40 g) eluted with methyl-tertbutyl-ether (3 vol) then 10% Methanol/ethyl acetate (60 vol). Fractions of interest were pooled and the solvent was removed under reduced pressure to give 5α-Hydroxy-6β-[2-(1H-imidazol-4-yl)-ethylamino]-cholest-7-en-3β-ol) as a white solid (7.2 g, 64%). In same conditions, use of ethanol as solvent (40 vol) and Ca(OTf)$_2$ as catalyst gave a 18% yield.

Example 12

5,6α-epoxicampestan-3β-ol (9.2 g, 22.1 mmol, 1 eq) and spermidine (6.4 g, 44.1 mmol, 2 eq) were charged in a round-bottomed flask equipped with a magnetic stirrer bar. 1-Butanol (70 ml, 5 vol) was added and the mixture heated to reflux for 40 h. The reaction mixture was cooled at r.t., diluted with methyl-tertbutyl-ether (5 vol) and washed with water (5 vol) and with brine (5 vol). The organic layer was passed through a silica pad (40 g) eluted with methyl-tertbutyl-ether (3 vol) then 10% Methanol/ethyl acetate (60 vol). Fractions of interest were pooled and the solvent was removed under reduced pressure to give 5α-Hydroxy-6β-[4-(3-aminopropylamino)-butylamino]-campestan-3,3-ol as a light yellow solid (4.8 g, 39%). In same conditions, use of ethanol as solvent (40 vol) and Ca(OTf)$_2$ as catalyst gave a 10% yield.

Example 13

5,6α-epoxisitostan-3β-ol (9.5 g, 22.1 mmol, 1 eq) and spermidine (6.4 g, 44.1 mmol, 2 eq) were charged in a round-bottomed flask equipped with a magnetic stirrer bar. 1-Butanol (70 ml, 5 vol) was added and the mixture heated to reflux for 40 h. The reaction mixture was cooled at r.t., diluted with methyl-tertbutyl-ether (5 vol) and washed with water (5 vol) and with brine (5 vol). The organic layer was passed through a silica pad (40 g) eluted with methyl-tertbutyl-ether (3 vol) then 10% Methanol/ethyl acetate (60 vol). Fractions of interest were pooled and the solvent was removed under reduced pressure to give 5α-Hydroxy-6β-[4-(3-aminopropylamino)-butylamino]-sitostan-3β-ol as a light yellow solid (6.5 g, 51%). In same conditions, use of ethanol as solvent (40 vol) and Ca(OTf)$_2$ as catalyst gave a 12% yield.

Example 14

5,6α-epoxicholest-7-en-3β-ol (8.9 g, 22.1 mmol, 1 eq) and 1,3-diaminopropane (3.3 g, 44.1 mmol, 2 eq) were charged in a round-bottomed flask equipped with a magnetic stirrer bar. 1-Butanol (70 ml, 5 vol) was added and the mixture heated to reflux for 40 h. The reaction mixture was cooled at r.t., diluted with methyl-tertbutyl-ether (5 vol) and washed with water (5 vol) and with brine (5 vol). The organic layer was passed through a silica pad (40 g) eluted with methyl-tertbutyl-ether (3 vol) then 10% Methanol/ethyl acetate (60 vol). Fractions of interest were pooled and the solvent was removed under reduced pressure to give 5α-Hydroxy-6β-(3-aminopropylamino)-cholest-7-en-3β-ol as a white solid (6.9 g, 66%). In same conditions, use of ethanol as solvent (40 vol) and Ca(OTf)$_2$ as catalyst gave a 21% yield.

Example 15

5,6α-epoxicholest-7-en-3β-ol (8.9 g, 22.1 mmol, 1 eq) and tryptamine (7.1 g, 44.1 mmol, 2 eq) were charged in a round-bottomed flask equipped with a magnetic stirrer bar. 1-Butanol (70 ml, 5 vol) was added and the mixture heated to reflux for 40 h. The reaction mixture was cooled at r.t., diluted with methyl-tertbutyl-ether (5 vol) and washed with water (5 vol) and with brine (5 vol). The organic layer was passed through a silica pad (40 g) eluted with methyl-tertbutyl-ether (3 vol) then 10% Methanol/ethyl acetate (60 vol). Fractions of interest were pooled and the solvent was removed under reduced pressure to give 5α-Hydroxy-6β-(3-propylamino)-cholest-7-en-3β-ol as a white solid (7.3 g, 59%). In same conditions, use of ethanol as solvent (40 vol) and Ca(OTf)$_2$ as catalyst gave a 23% yield.

Example 16

5,6α-epoxicholest-7-en-3β-ol (8.9 g, 22.1 mmol, 1 eq) and N$^1$,N$^8$-di-tert-butyloxycarbonyl-spermidine (15.2 g, 44.1 mmol, 2 eq) were charged in a round-bottomed flask equipped with a magnetic stirrer bar. 1-Butanol (70 ml, 5 vol) was added and the mixture heated to reflux for 40 h. The reaction mixture was cooled at r.t., diluted with methyl-tertbutyl-ether (5 vol) and washed with water (5 vol) and with brine (5 vol). The organic layer was passed through a silica pad (40 g) eluted with methyl-tertbutyl-ether (3 vol) then 10% Methanol/ethyl acetate (60 vol). Fractions of interest were pooled and the solvent was removed under reduced pressure to give 5α-Hydroxy-6β-[(4-tertbutyloxycarbonylaminobutyl)-(3-tertbutyloxycarbonylaminopropyl)-amino]-cholest-7-en-3β-ol as a white solid (9.9 g, 60%). In same conditions, use of ethanol as solvent (40 vol) and Ca(OTf)$_2$ as catalyst gave a 15% yield.

Example 17

5,6α-epoxicholestan-3β-ol (8.9 g, 22.1 mmol, 1 eq) and N$^1$,N$^8$-di-tert-butyloxycarbonyl-spermidine (15.2 g, 44.1 mmol, 2 eq) were charged in a round-bottomed flask equipped with a magnetic stirrer bar. 1-Butanol (70 ml, 5 vol) was added and the mixture heated to reflux for 40 h. The reaction mixture was cooled at r.t., diluted with methyl-tertbutyl-ether (5 vol) and washed with water (5 vol) and with brine (5 vol). The organic layer was passed through a silica pad (40 g) eluted with methyl-tertbutyl-ether (3 vol) then 10% Methanol/ethyl acetate (60 vol). Fractions of interest were pooled and the solvent was removed under reduced pressure to give 5α-Hydroxy-6β-[(4-tertbutyloxycarbonylaminobutyl)-(3-tertbutyloxycarbonylaminopropyl)-amino]-cholestan-3β-ol as a white solid (9.1 g, 55%). In same conditions, use of ethanol as solvent (40 vol) and Ca(OTf)$_2$ as catalyst gave a 12% yield.

Example 18

5,6α-epoxicholestan-3β-yl acetate (9.8 g, 22.1 mmol, 1 eq) and histamine (4.9 g, 44.1 mmol, 2 eq) were charged in a round-bottomed flask equipped with a magnetic stirrer bar. 1-Butanol (70 ml, 5 vol) was added and the mixture heated to reflux for 40 h. The reaction mixture was cooled at r.t., diluted with methyl-tertbutyl-ether (5 vol) and washed with water (5 vol) and with brine (5 vol). The organic layer was passed through a silica pad (40 g) eluted with methyl-tertbutyl-ether (3 vol) then 10% Methanol/ethyl acetate (60 vol). Fractions of interest were pooled and the solvent was removed under reduced pressure to give 5α-Hydroxy-6β-[2-(1H-imidazol-4-yl)-ethylamino]-cholestan-3β-yl acetate as a white solid (7.5 g, 58%). In same conditions, use of ethanol as solvent (40 vol) and Ca(OTf)$_2$ as catalyst gave a 14% yield.

Example 19

5,6α-epoxicholestan-3β-yl butyrate (10.4 g, 22.1 mmol, 1 eq) and histamine (4.9 g, 44.1 mmol, 2 eq) were charged in a round-bottomed flask equipped with a magnetic stirrer bar. 1-Butanol (70 ml, 5 vol) was added and the mixture heated to reflux for 40 h. The reaction mixture was cooled at r.t., diluted with methyl-tertbutyl-ether (5 vol) and washed with water (5 vol) and with brine (5 vol). The organic layer was passed through a silica pad (40 g) eluted with methyl-tertbutyl-ether (3 vol) then 10% Methanol/ethyl acetate (60 vol). Fractions of interest were pooled and the solvent was removed under reduced pressure to give 5α-Hydroxy-6β-[2-(1H-imidazol-4-yl)-ethylamino]-cholestan-3β-yl butyrate as a white solid (7.8 g, 57%). In same conditions, use of ethanol as solvent (40 vol) and Ca(OTf)$_2$ as catalyst gave a 13% yield.

Example 20

5,6α-epoxicholestan-3β-ol (8.9 g, 22.1 mmol, 1 eq) and ethanolamine (2.7 ml, 44.1 mmol, 2 eq) were charged in a round-bottomed flask equipped with a magnetic stirrer bar. 1-Butanol (70 ml, 5 vol) was added and the mixture heated to reflux for 40 h. The reaction mixture was cooled at r.t., diluted with methyl-tertbutyl-ether (5 vol) and washed with water (5 vol) and with brine (5 vol). The organic layer was passed through a silica pad (40 g) eluted with methyl-tertbutyl-ether (3 vol) then 10% Methanol/ethyl acetate (60 vol). Fractions of interest were pooled and the solvent was removed under reduced pressure to give 5α-Hydroxy-6β-[2-hydroxyethylamino]-cholestan-3β-ol as a white solid (9.4 g, 98%). In same conditions, use of ethanol as solvent (40 vol) and Ca(OTf)$_2$ as catalyst gave a 17% yield.

Comparative Example 1

5,6α-epoxicholestan-3β-ol (8.9 g, 22.1 mmol, 1 eq) and histamine (4.9 g, 44.1 mmol, 2 eq) were charged in a round-bottomed flask equipped with a magnetic stirrer bar. 1-Butanol (70 ml, 5 vol) was added and the mixture stirred at room temp for 40 h. TLC of the reaction mixture showed no transformation products.

Comparative Example 2

5,6α-epoxicholestan-3β-ol (8.9 g, 22.1 mmol, 1 eq) and histamine (4.9 g, 44.1 mmol, 2 eq) were charged in a round-bottomed flask equipped with a magnetic stirrer bar. 1-propanol (70 ml, 5 vol) was added and the mixture stirred at room temp for 40 h. TLC of the reaction mixture showed no transformation products.

Comparative Example 3

5,6α-epoxicholestan-3β-ol (8.9 g, 22.1 mmol, 1 eq) and histamine (4.9 g, 44.1 mmol, 2 eq) were charged in a round-bottomed flask equipped with a magnetic stirrer bar. 1-propanol (70 ml, 5 vol) then Ca(OTf)$_2$ (3 eq) were added and the mixture stirred at room temp for 40 h. TLC of the reaction mixture showed no transformation products.

The invention claimed is:
1. A process for the preparation of a compound of formula (I):

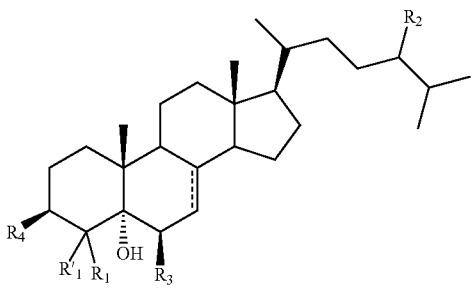

wherein:
the dotted line denotes a bond which is single or double,
$R_1$ and $R'_1$ are the same or different and represent H or $CH_3$,
$R_2$ is H, $CH_3$ or $C_2H_5$,
$R_3$ is —NRR' wherein R and R' are the same or different and are selected from the group consisting of:
—H,
—$(CH_2)$n-OH wherein
n is an integer comprised between 1 and 4,
—$(CH_2)$n-NHP wherein
n is an integer comprised between 1 and 6 and
P is H or a protecting group;
—$(CH_2)$n-NP—$(CH_2)$m-NHP' wherein
n is an integer comprised between 1 and 6,
m is an integer comprised between 1 and 6, and
P and P' are the same or different and represent H or a protecting group;
—$(CH_2)$n-NP—$(CH_2)$m-NP'—$(CH_2)$p-NHP'' wherein
n is an integer comprised between 1 and 6,
m is an integer comprised between 1 and 6,
p is an integer comprised between 1 and 6, and
P, P' and P'' are the same or different and represent H or a protecting group;
—$(CH_2)$n-X wherein
n is an integer comprised between 1 and 4 and
X=imidazol, indol or phenyl, optionally substituted with one or several groups selected from the group consisting of OH, $NH_2$ and SH;
$R_4$ is OH, acetoxy or butoxy,
said process comprising:
(a) reacting an α-epoxy compound of formula (II):

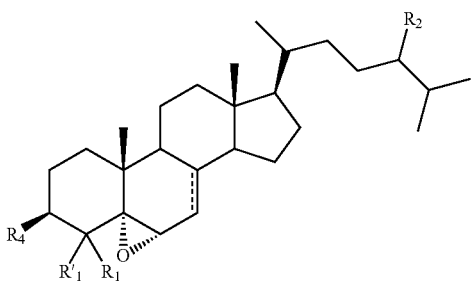

wherein $R_1$, $R'_1$, $R_2$, and $R_4$ have the same meaning as in formula (I) and the dotted line denotes a bond which is single or double, with a monoamine or polyamine of formula (III):

$R_3H$         (III)

wherein $R_3$ has the same meaning as in formula (I)
in a reaction medium at reflux;
(b) recovering compound (I) from the reaction medium;
wherein a 3 to 5 carbon atom alcohol or a mixture of 3 to 5 carbon atom alcohols is used as a solvent in the reaction medium.

2. The process for the preparation of a compound of formula (I) according to claim 1, wherein the alcohol is selected from the group consisting of 1-propanol, 1-butanol and 2-butanol.

3. The process for the preparation of a compound of formula (I) according to claim 1, wherein the amine of formula (III) is a monoamine or polyamine of formula NHR wherein R is selected from the group consisting of:
—$(CH_2)$n-OH wherein
n is an integer comprised between 1 and 4,
—$(CH_2)$n-NHP wherein
n is an integer comprised between 1 and 6 and
P is H or a protecting group;
—$(CH_2)$n-NP—$(CH_2)$m-NHP' wherein
n is an integer comprised between 1 and 6,
m is an integer comprised between 1 and 6, and
P and P' are the same or different and represent H or a protecting group;
—$(CH_2)$n-NP—$(CH_2)$m-NP'—$(CH_2)$p-NHP'' wherein
n is an integer comprised between 1 and 6,
m is an integer comprised between 1 and 6,
p is an integer comprised between 1 and 6, and
P, P' and P'' are the same or different and represent H or a protecting group;
—$(CH_2)$n-X wherein
n is an integer comprised between 1 and 4 and
X=imidazol, indol or phenyl, optionally substituted with one or several groups selected from the group consisting of OH, $NH_2$ and SH.

4. The process for the preparation of a compound of formula (I) according to claim 1, wherein the amine of formula (III) is a monoamine or polyamine of formula NHR wherein R is selected from the group consisting of:
—$(CH_2)$n-OH wherein
n is an integer comprised between 1 and 4,
—$(CH_2)$n-NHP wherein
n is an integer comprised between 1 and 4 and
P is H or a protecting group;
—$(CH_2)$n-NP—$(CH_2)$m-NHP' wherein
n is an integer comprised between 1 and 4,
m is an integer comprised between 1 and 4, and
P and P' are the same or different and represent H or a protecting group;
—$(CH_2)$n-NP—$(CH_2)$m-NP'—$(CH_2)$p-NHP'' wherein
n is an integer comprised between 1 and 4,
m is an integer comprised between 1 and 4,
p is an integer comprised between 1 and 4, and
P, P' and P'' are the same or different and represent H or a protecting group;
—$(CH_2)$n-X wherein
n is an integer comprised between 1 and 4 and
X=imidazol, indol or phenyl, optionally substituted with one or several groups selected from the group consisting of OH, $NH_2$ and SH.

5. The process for the preparation of a compound of formula (I) according to claim 1, wherein the amine of formula (III) is selected from the group consisting of histamine, spermidine, spermine, putrescine, ethanolamine, diaminopropylamine, diaminobutylamine, tryptamine, serotonin, 1,3-diaminopropane, and $N^1,N^8$-di-tert-butyloxycarbonylspermidine.

6. The process for the preparation of a compound of formula (I) according to claim 1, wherein the compound of formula (II) is selected from the group consisting of cholestan-5α,6α-epoxy-3β-ol, cholesten-5α,6α-epoxy-3β-ol, sitostan-5α,6α-epoxy-3β-ol, campestan-5α,6α-epoxy-3β-ol, 3β-acetoxy-cholestan-5α,6α-epoxide, 3β-acetoxy-sitostan-5α,6α-epoxide and 3β-acetoxy-campestan-5α,6α-epoxide.

7. The process for the preparation of a compound of formula (I) according to claim 1, wherein the reaction medium is devoid of any catalyst.

8. The process for the preparation of a compound of formula (I) according to claim 1, wherein the reaction medium comprises a catalyst.

9. The process for the preparation of a compound of formula (I) according to claim 1, wherein compound (I) is:
  5α-hydroxy-6β-[2-(1H-imidazol-4-yl)ethylamino]cholestan-3β-ol,
  5α-hydroxy-6β-[2-(1H-imidazol-4-yl)ethylamino]campestan-3β-ol,
  5α-hydroxy-6β-[2-(1H-imidazol-4-yl)ethylamino]sitostan-3β-ol,
  3β-acetoxy-5α-hydroxy-6β-[2-(1H-imidazol-4-yl)ethylamino]cholestane,
  3β-acetoxy-5α-hydroxy-6β-[2-(1H-imidazol-4-yl)ethylamino]campestane,
  3β-acetoxy-5α-hydroxy-6β-[2-(1H-imidazol-4-yl)ethylamino]sitostane,
  5α-hydroxy-6β-[2-(1H-indol-3-yl)ethylamino]cholestan-3β-ol,
  5α-hydroxy-6β-[2-(1H-indol-3-yl)ethylamino]campestan-3β-ol,
  5α-hydroxy-6β-[2-(1H-indol-3-yl)ethylamino]sitostan-3β-ol,
  5α-hydroxy-6β-[2-(1H-indol-3-yl)ethylamino]cholest-7-en-3β-ol,
  3β-acetoxy-5α-hydroxy-6β-[2-(1H-indol-3-yl)ethylamino]cholestane,
  3β-acetoxy-5α-hydroxy-6β-[2-(1H-indol-3-yl)ethylamino]campestane,
  3β-acetoxy-5α-hydroxy-6β-[2-(1H-indol-3-yl)ethylamino]sitostane,
  3β-acetoxy-5α-hydroxy-6β-[2-(1H-indol-3-yl)ethylamino]cholest-7-ene,
  5α-hydroxy-6β-[2-(1H-indol-3-yl-5-ol)ethylamino]cholestan-3β-ol,
  5α-hydroxy-6β-[2-(1H-indol-3-yl-5-ol)ethylamino]cholest-7-en-3β-ol,
  5α-hydroxy-6β-[2-(1H-indol-3-yl-5-ol)ethylamino]campestan-3β-ol,
  5α-hydroxy-6β-[2-(2-(1H-indol-3-yl-5-ol)ethylamino]sitostan-3β-ol,
  3β-acetoxy-5α-hydroxy-6β-[2-(2-(1H-indol-3-yl-5-ol)ethylamino]cholestane,
  3β-acetoxy-5α-hydroxy-6β-[2-(1H-indol-3-yl-5-ol)ethylamino]cholest-7-ene,
  3β-acetoxy-5α-hydroxy-6β-[2-(2-(1H-indol-3-yl-5-ol)ethylamino]campestane,
  3β-acetoxy-5α-hydroxy-6β-[2-(1H-indol-3-yl-5-ol)ethylamino]sitostane,
  5α-hydroxy-6β-[3-(4-aminobutylamino)propylamino]cholest-7-en-3β-ol,
  5α-hydroxy-6β-[4-(3-aminopropylamino)butylamino]cholest-7-en-3β-ol,
  5α-hydroxy-6β-[3-(4-aminobutylamino)propylamino]cholestan-3β-ol,
  5α-hydroxy-6β-[4-(3-aminopropylamino)butylamino]cholestan-3β-ol,
  5α-hydroxy-6β-[3-(4-aminobutylamino)propylamino]campestan-3β-ol,
  5α-hydroxy-6β-[4-(3-aminopropylamino)butylamino]campestan-3β-ol,
  5α-hydroxy-6β-[3-(4-aminobutylamino)propylamino]sitostan-3β-ol,
  5α-hydroxy-6β-[4-(3-aminopropylamino)butylamino]sitostan-3β-ol,
  5α-hydroxy-6β-[(4-aminobutyl)(3-aminopropylamino)]cholest-7-en-3β-ol,
  5α-hydroxy-6β-[(4-aminobutyl)(3-aminopropylamino)]cholestan-3β-ol,
  5α-hydroxy-6β-[(4-aminobutyl)(3-aminopropylamino)]campestan-3β-ol,
  5α-hydroxy-6β-[(4-aminobutyl)(3-aminopropylamino)]sitostan-3β-ol,
  5α-hydroxy-6β-{3-[4-(3-aminopropylamino)butylamino]propylamino}cholest-7-en-3β-ol,
  5α-hydroxy-6β-{3-[4-(3-aminopropylamino)butylamino]propylamino}cholestan-3β-ol,
  5α-hydroxy-6β-{3-[4-(3-aminopropylamino)butylamino]propylamino}campestan-3β-ol,
  5α-hydroxy-6β-{3-[4-(3-aminopropylamino)butylamino]propylamino}sitostan-3β-ol,
  5α-hydroxy-6β-(4-aminobutylamino)cholest-7-en-3β-ol,
  5α-hydroxy-6β-(4-aminobutylamino)cholestan-3β-ol,
  5α-hydroxy-6β-(4-aminobutylamino)campestan-3β-ol,
  5α-hydroxy-6β-(4-aminobutylamino)sitostan-3β-ol,
  5α-hydroxy-6β-(3-aminopropylamino)cholest-7-en-3β-ol,
  5α-hydroxy-6β-(3-aminopropylamino)cholestan-3β-ol,
  5α-hydroxy-6β-(3-aminopropylamino)campestan-3β-ol,
  5α-hydroxy-6β-(3-aminopropylamino)sitostan-3β-ol,
  3β-acetoxy-5α-hydroxy-6β-[3-(4-aminobutylamino)propylamino]cholest-7-ene,
  3β-acetoxy-5α-hydroxy-6β-[4-(3-aminopropylamino)butylamino]cholest-7-ene,
  3β-acetoxy-5α-hydroxy-6β-[3-(4-aminobutylamino)propylamino]cholestane,
  3β-acetoxy-5α-hydroxy-6β-[4-(3-aminopropylamino)butylamino]cholestane,
  3β-acetoxy-5α-hydroxy-6β-[3-(4-aminobutylamino)propylamino]campestane,
  3β-acetoxy-5α-hydroxy-6β-[4-(3-aminopropylamino)butylamino]campestane,
  3β-acetoxy-5α-hydroxy-6β-[3-(4-aminobutylamino)propylamino]sitostane,
  3β-acetoxy-5α-hydroxy-6β-[4-(3-aminopropylamino)butylamino]sitostane,
  3β-acetoxy-5α-hydroxy-6β-[(4-aminobutyl)(3-aminopropylamino)]cholest-7-ene,
  3β-acetoxy-5α-hydroxy-6β-[(4-aminobutyl)(3-aminopropylamino)]cholestane,
  3β-acetoxy-5α-hydroxy-6β-[(4-aminobutyl)(3-aminopropylamino)]campestane,
  3β-acetoxy-5α-hydroxy-6β-[(4-aminobutyl)(3-aminopropylamino)]sitostane,
  3β-acetoxy-5α-hydroxy-6β-{3-[4-(3-aminopropylamino)butylamino]propylamino}cholest-7-ene,
  3β-acetoxy-5α-hydroxy-6β-{3-[4-(3-aminopropylamino)butylamino]propylamino}cholestane,
  3β-acetoxy-5α-hydroxy-6β-{3-[4-(3-aminopropylamino)butylamino]propylamino}campestane, 3β-acetoxy-5α-hydroxy-6β-{3-[4-(3-aminopropylamino) butylamino]propylamino}sitostane, 3β-acetoxy-5α-hydroxy-6β-(4-aminobutylamino) cholest-7-ene, 3β-acetoxy-5α-hydroxy-6β-(4-aminobutylamino)cholestane, 3β-acetoxy-5α-hydroxy-6β-(4-aminobutylamino) campestane, 3β-acetoxy-5α-hydroxy-6β-(4-aminobutylamino)sitostane, 3β-acetoxy-5α-hydroxy-6β-(3-aminopropylamino) cholest-7-ene, 3β-acetoxy-5α-hydroxy-6β-(3-aminopropylamino) cholestane, or 3β-acetoxy-5α-hydroxy-6β-(3-aminopropylamino) campestane.

10. The process for the preparation of a compound of formula (I) according to claim 1, wherein the compound recovered from step b) contains at least one amino protecting group and is further reacted with a deprotecting agent so as to remove said amino protecting group from the compound.

11. The process for the preparation of a compound of formula (I) according to claim 1, wherein the α-epoxy compound of formula (II) is obtained by:

a) reacting meta-chloroperoxybenzoic acid with a compound of formula (IV):

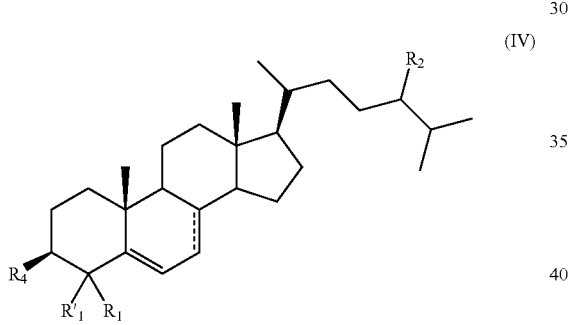

wherein $R_1$, $R'_1$, $R_2$, and $R_4$ have the same meaning than in formula (I) and the dotted line denotes a bond which is single or double;

b) recovering said α-epoxy compound of formula (II).

12. The process for the preparation of a compound of formula (I) according to claim 11, wherein compound of formula (IV) is selected from the group consisting of cholesterol, sitosterol, campesterol, 7-dehydrocholesterol, 7-dehydrositosterol and 7-dehydrocampesterol.

13. A process for the preparation of Dendrogenin A of formula:

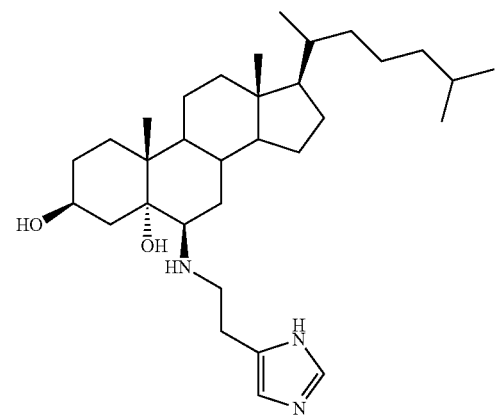 [SMILES: CC(C)CCCC(C)[C@H]1CCC2C3C[C@@H](NCCc4cnc[nH]4)[C@@]4(O)C[C@@H](O)CC[C@]4(C)C3CC[C@@]21C]

said process comprising:

(a) reacting 5,6α-epoxicholestan-3β-ol epoxide with histamine in a reaction medium at reflux;

(b) recovering Dendrogenin A from the reaction medium; wherein 1-butanol is used as a solvent in the reaction medium.

14. A process for the preparation of Dendrogenin B of formula:

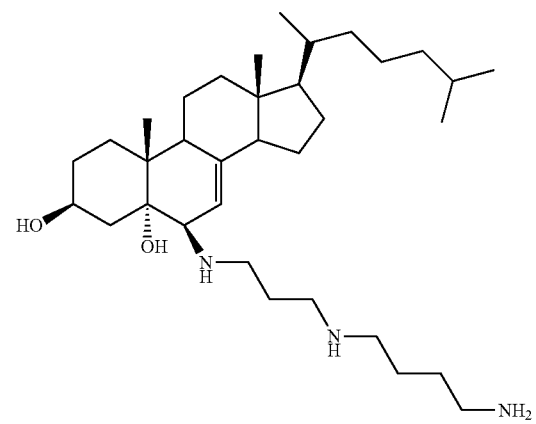 [SMILES: CC(C)CCCC(C)[C@H]1CCC2C3=C[C@@H](NCCCNCCCCN)[C@@]4(O)C[C@@H](O)CC[C@]4(C)C3CC[C@@]21C]

said process comprising:

(a) reacting 5,6α-epoxicholest-7-en-3β-ol with spermidine in a reaction medium at reflux;

(b) recovering Dendrogenin B from the reaction medium; wherein 1-butanol is used as a solvent in the reaction medium.

15. The process of claim 8, wherein the catalyst is selected from the group consisting of $LiClO_4$, $Sc(OTf)_3$, $Tb(OTf)_3$, and $Ca(OTf)_2$.

* * * * *